US008705826B2

(12) United States Patent
Liu et al.

(10) Patent No.: US 8,705,826 B2
(45) Date of Patent: Apr. 22, 2014

(54) AUTOMATIC CUP-TO-DISC RATIO MEASUREMENT SYSTEM

(75) Inventors: Jiang Liu, Terrace (SG); Joo Hwee Lim, Terrace (SG); Wing Kee Wong, Terrace (SG); Huiqi Li, Terrace (CN); Tien Yin Wong, SNEC Building (SG)

(73) Assignee: Agency for Science, Technology and Research, Centros (SG)

( * ) Notice: Subject to any disclaimer, the term of this patent is extended or adjusted under 35 U.S.C. 154(b) by 360 days.

(21) Appl. No.: 12/992,299

(22) PCT Filed: May 14, 2008

(86) PCT No.: PCT/SG2008/000186
§ 371 (c)(1),
(2), (4) Date: Nov. 12, 2010

(87) PCT Pub. No.: WO2009/139722
PCT Pub. Date: Nov. 19, 2009

(65) Prior Publication Data
US 2011/0091083 A1   Apr. 21, 2011

(51) Int. Cl.
*G06K 9/00* (2006.01)
(52) U.S. Cl.
USPC ........................................... 382/131; 382/157
(58) Field of Classification Search
None
See application file for complete search history.

(56) References Cited

U.S. PATENT DOCUMENTS

| | | | |
|---|---|---|---|
| 6,030,079 A | | 2/2000 | Torii |
| 7,524,061 B2 * | | 4/2009 | Yan et al. .................. 351/206 |
| 2002/0052551 A1 * | | 5/2002 | Sinclair et al. ............. 600/476 |
| 2004/0105074 A1 * | | 6/2004 | Soliz et al. ................. 351/206 |
| 2007/0230795 A1 * | | 10/2007 | Abramoff et al. ........... 382/190 |
| 2008/0097794 A1 * | | 4/2008 | Arnaud et al. ............... 705/3 |
| 2008/0309881 A1 * | | 12/2008 | Huang et al. ............... 351/246 |
| 2009/0268159 A1 * | | 10/2009 | Xu et al. .................... 351/206 |

FOREIGN PATENT DOCUMENTS

FR           2907327 A1    4/2008

OTHER PUBLICATIONS

Sharma, "Automated depth analysis of optic nerve head from stereo fundus images", Thesis, Texas Tech University (May 2006).
Jayasundera et al., "Agreement between stereoscopic photographs, clinical assessment, Heidelberg retina tomograph . . .", 33 Brit. J. Ophthalmology (2005), pp. 259-262.
Garway-Heath et al., "Vertical cup/disc ration in relation to optic disc size: its value in the assessment of the glaucoma suspect", 82 Brit. J. Ophthalmology (1998), pp. 1118-1124.

(Continued)

*Primary Examiner* — Jingge Wu
(74) *Attorney, Agent, or Firm* — Bracewell & Giuliani LLP

(57) ABSTRACT

A two-dimensional retinal fundus image of the retinal fundus of an eye is processed by optic disc segmentation (2) followed by cup segmentation 4. Data derived from the optic disc segmentation (i.e. the output of the disc segmentation (2) and/or data derived from the output of the optic disc segmentation step, e.g. by a smoothing operation 3) and data derived from the out-put of the optic cup segmentation (i.e. the output of the cup segmentation (4) and/or data derived from the output of the optic disc segmentation, e.g. by a smoothing operation 5) are fed (6) to an adaptive model which has been trained to generate from such inputs a value indicative of cup-to-disc ratio (CDR) of the eye. The CDR is indicative of glaucoma. Thus, the method can be used to screen patients for glaucoma.

24 Claims, 3 Drawing Sheets

(56) References Cited

OTHER PUBLICATIONS

Arthur et al., "Agreement in assessing cup-to-disc ratio measurement among stereoscopic optic nerve head photographs, HRT II, and Stratus OCT", 15(3) J. Glaucoma (Jun. 2006), pp. 183-189.

Watkins et al., "Vertical cup-to-disc ratio: Agreement between direct ophthalmoscopic estimation, and scanning laser ophthalmoscopic measurement", 80(6) Optom, & Vision Sci. (Jun. 2003), pp. 454-459.

Beaumont et al., "Cup-to-disc ratio, intraocular pressure, and primary open-angle glaucoma in retinal venous occlusion", 109(2) Amer. Aca. Ophth. (Feb. 2002), pp. 282-286.

International Search Report (PCT/SG2008/000186), filed Jul. 7, 2020.

Li et al., "A model-based approach for automated feature extraction in fundus images", Proc. 9th IEEE Int'l Conf. on Computer Vision (2003).

Tang et al., "Automatic segmentation of the papilla in a fundus image based on the C-V model and a shape restraint", Proc. 18th Int'l Conf. on Pattern Recognition (2006).

Inoue et al., "Development of a simple diagnostic method for the glaucoma using ocular fundus pictures", Proc. 27th IEEE Engineering in Med. & Biol. Ann. Conf. (2005).

Xu et al., "Optic disc feature extraction via modified deformable model technique for glaucoma analysis", Pattern Recognition 40 (2007), pp. 2062-2076.

Li et al., "Level set evolution without re-initialization: a new variational formulation", Proc. 2005 IEEE Computer Soc. Conf. on Computer Vision and Pattern Recognition (2005).

EP Search Report (EP 08754024.1), dated May 21, 2012.

Inoue et al., "Development of a simple diagnostic method for the glaucoma using ocular Fundus pictures", Proc. of 2005 IEEE, Engineering in Medicine & Biol 27th Annual Conference, Shanghai, China (Sep. 1-4, 2005), pp. 3355-3358.

Liu et al. "Reconstruction Segmentation and Measurement of the Color Optic Cup and Disk Image of Optic Nerve Heads Based on Hierarchical Mumford-Shah Model", 26(5) Chinese J. Biomed. Engin. (Oct. 2007), pp. 700-712.

Martinello et al., Abstract—"3-D retinal surface inference: stereo or monocular fundus camera?", Conf. Proc. IEEE Eng Med. Biol. Soc. (2007), pp. 896-899, retrieved from www.ncbi.nlm.nih.gov/pubmed/18002101, dated Mar. 20, 2013.

Project Summary—"Retinal Imaging: Monocular or Stereo Fundus Camera?", retrieved from visp.eps.hw.ac.uk/-pf21/pages/page1/page1.html, dated Mar. 21, 2013.

Liew, Gerald, et al., The Retinal Vasculature as a Fractal: Methodology, Reliability, and Relationship to Blood Pressure, Available online Aug. 9, 2008, pp. 1951-1956, American Academy of Ophthalmology.

Cheung, Ning, et al., Quantitative Assessment of Early Diabetic Retinopathy Using Fractal Analysis, Diabetes Care, Jan. 2009, pp. 106-110, vol. 32, No. 1.

\* cited by examiner (a) (b)

AUTOMATIC CUP-TO-DISC RATIO MEASUREMENT SYSTEM

RELATED APPLICATION

This application claims priority to PCT application PCT/SG2008/000186 filed May 14, 2008.

FIELD OF THE INVENTION

The present invention relates to a system, having method and apparatus aspects, for automatically measuring a ratio of respective diameters of the optical disc cup (also referred to herein as an "optic cup") and the optical disc of an eye. That is, the eye's "cup-disc-ratio" (CDR). This measurement may be employed in glaucoma detection or analysis.

BACKGROUND OF THE INVENTION

Glaucoma is a leading cause of blindness and is characterized by the progressive loss of axons in the optic nerve. According to the World Health Organisation's Global Data Bank on Blindness, glaucoma accounts for 5.1 million out of an estimated 38 million blind people, or about 13.4%, worldwide. As the world's population rapidly ages, glaucoma morbidity will rise, resulting in increased health care costs and economic burden. There is no cure for glaucoma, as damage to the axons is permanent and as yet is irrecoverable. However, with early detection, the advancement of glaucomatous optical neuropathy can be significantly slowed or even halted. Mass screening is thus critical to prevent the further development of glaucomatous damage. However, no ideal community-based screening test has been found. Such a test would be beneficial for diagnostic as well as therapeutic purposes. Glaucomatous optic nerve damage precedes clinical identifiable visual loss, so early detection of glaucoma optic nerve damage through medical imaging technology would help ophthalmologists to identify, monitor and discover new ways to manage patients and slow the progression of the condition. This test should ideally be clinician-independent, rapid, non-invasive and have a very high specificity.

A classic feature of glaucoma is the specific abnormal appearance of the optic nerve head: cupping or excavation of the optic disc, with loss of the neuroretinal rim, typically seen as an enlargement of the optic disc cup to disc ratio (CDR). FIG. 1 shows enlargement of the optic cup and increase in the CDR over a 10 year period. FIG. 1(a) shows a normal eye, and FIG. 1(b) the same eye after 10 years. The central bright area of FIG. 1(a) is the optic cup, while the well-defined ellipse is the disc. As shown in FIG. 1(b), the optic cup has gradually enlarged to fill much of the disc. The CDR is regarded as an important indicator for detecting the presence of glaucoma in a patient, as well as the extent of glaucomatous optical neuropathy. In current clinical practice, the CDR is measured manually by an ophthalmologist and is subjective due to differences in the intra-observer experiences and training. The reliance on manual efforts restricts the use of the CDR for deployment in mass screening.

There are currently 3 main medical imaging modalities for glaucoma diagnosis: retinal fundus photography, optical coherence tomography (OCT) and Heidelberg Retinal Tomography (HRT).

Retinal fundus photography makes use of a fundus camera to capture images of the retinal fundus, including the optic disc and is currently the standard employed approach for observing and diagnosing ocular maladies. The camera is based on the principle of monocular indirect ophthalmoscopy.

OCT is an interferometric, non-invasive optical tomographic imaging technology capable of achieving sub-micrometer resolution due to its cross-sectional imaging capabilities. HRT is a confocal laser scanning system designed for acquisition and analysis of 3D images of the posterior segment. HRT enables the quantitative assessment of the topography of ocular structure and the precise follow-up of the topographic changes. However, OCT and HRT systems suffer numerous disadvantages. Firstly, they are expensive and require a greater expertise to operate when compared with the retinal photography-based systems. The effectiveness of OCT for glaucoma diagnosis is restricted by the technology's limited depth penetration and lack of true color data. The Image quality obtained via OCT is also dependent on operator technique and can be degraded in the presence of media opacity. Some parameters obtained with OCT may be affected by structural changes around the optic disc head. Change analysis software for glaucoma applications is not fully developed, and there is a scarcity of age, gender, and race-specific normative data upon which to compare eyes with retinal disease and glaucoma. For HRT, although the test only requires a few seconds to perform, the results are extremely sensitive to patient movements, including eye and head movements, and blinks, disrupting the laser's path, and impairing the quality of the obtained image.

In attempting to make use of retinal fundus images, researchers have focused their efforts on the automatic segmentation of the optic disc. However, there have been much less research work towards the detection of the optic cup due to the cup's interweavement with blood vessel and surrounding tissues.

In a first prior art reference [1], optic disc shape detection is done using a "modified" active shape model (ASM). It reaches a disc boundary detection rate of 94% on 100 datasets collected by the authors. No cup or CDR calculation were done in this paper. ASM is a searching procedure in which a "shape model" (a smooth shape in the image space defined by a plurality of parameters) is fitted to data, to produce a model termed a point distribution model (PDM). Modified ASM (as described below) improves conventional active shape models by adding a self-adjusting weight, and excluding the outlying points from the images. Specifically, a set of n "landmark points" is defined on the image. These points are transformed into "shape space" by a transform based on the numerical parameters of the model. For each landmark point, a corresponding "matching point" is found using a first derivative of the image intensity (or, in the case of a part of the disc boundary which is not well-defined because of blood vessels in the image, based on nearby matching points or landmark points), and the landmark points are then updated also using an energy function. This process is repeated iteratively. Writing the set of "matching points" in a given iteration as $Y=\{Y_i\}$ for $i=1,\ldots n$, a corresponding set of updated landscape points $\{X_i\}$ is produced by minimizing the energy function:

$$E_T = \sum_{i=1}^{n} (Y_i - X_i)^T W_i (Y_i - X_i) \quad (1.2.1)$$

It is the set of parameters $W_i$ which cause the modification of standard ASM. The function (1.2.1) is minimized twice with respect to the set of values $X_i$ in each iteration. The first time, the set of parameters $W_i$ is initialized to $$W_i = \begin{cases} 1 & Y_i \text{ is detected directly} \\ 0.7 & Y_i \text{ is estimated by nearby matching points} \\ 0 & Y_i \text{ is updated by } X_i \end{cases}$$

Setting $W_i$ to zero for some values of i eliminates the effect of points for which neither $Y_i$ nor nearby matching points can be detected. The second time, $W_i$ is adjusted to be the following:

$$W_i = \begin{cases} 1 & E_i < 5 \\ 5/E_i & 5 \le E_i \le 15 \\ 1/E_i & E_i > 15 \end{cases}$$

where $E_i$ is the Euclidean distance between $X_i$ and $Y_i$, and the function 1.2.1 is minimized again.

A second prior art reference [2] is based on the Chan-Vese (C-V) model for segmentation introduced by Tony Chan and Luminita Vese. This achieved Optic disc detection of 94% using a database containing 50 color fundus images, including 20 low contrast ones. This approach is formulated by defining a 'fitting energy' function E as the integral over the image space of a Lipschitz function $\phi(x, y)$ of coordinates (x, y) in the image space, and minimizing the fitting energy with respect to $\phi(x, y)$ subject to an elliptic shape restraint. No Cup and CDR calculation were done in this paper.

A third prior art reference [3] describes using discriminatory analysis to decide thresholds, and subsequently utilizes these to segment the cup and disc. Although the Cup-to-Disc Ratio (CDR) was measured in this paper, no clear results are given and the image sets used for testing are not clearly described.

A fourth prior art reference [4], describes disc and cup segmentation and CDR calculation. The optic disc center is found by applying the Circular Hough Transformation, and subsequently the disc boundary detection is done through an active shape model (ASM) by defining 72 points around the disc first. Finally, a first energy function is used to deform the contour to the best shape. The energy function depends on five energy terms weighted by respective parameters. Cup detection employs an initial estimate based on the disc contour detected earlier, and then deforms this using a second energy function. This method achieves the following mean and standard deviation of the percentage error rates, as shown in Table I:

TABLE I

Performance statistics of prior art reference [4]

| Metric | Value |
| --- | --- |
| Mean percentage error in finding CDR | −4.334012789 |
| Standard deviation percentage error | 12.59088846 |

SUMMARY OF THE INVENTION

The present invention seeks to provide a new and useful way of obtaining a CDR value from a fundus image.

In general terms, the invention proposes that a 2D retinal fundus image is processed by a step of optic disc segmentation followed by a step of cup segmentation. Data derived from the optic disc segmentation step (i.e. the output of the disc segmentation step and/or data derived from the output of the optic disc segmentation step, e.g. by a smoothing operation) and data derived from the output of the optic cup segmentation step (i.e. the output of the cup segmentation step and/or data derived from the output of the optic disc segmentation step, e.g. by a smoothing operation) are fed to an adaptive model which has been trained to generate from such inputs a value indicative of CDR.

Thus, certain embodiments of the invention are able automatically to calculate a CDR value from retinal photographs, providing a fast, objective and consistent measurement with potential for mass screening of populations.

Typically the cup segmentation is performed using data derived from the result of said optic disc segmentation, although in principle it would be possible to perform the cup segmentation independently.

The training of the adaptive model employs training data including target CDR values obtained by clinical practitioners. Thus, the invention may permit clinical knowledge to be incorporated straightforwardly in the construction of the system.

Experimentally, it has been found that an embodiment of the method (referred to below as "Automatic cup-to-disc Ratio measurement for Glaucoma detection and AnaLysIs", or "ARGALI") is able to provide a rapid and accurate value of CDR, and may thus be employed as a tool in a diagnostic system for glaucoma screening. Since 2D retinal fundus images can be obtained through the use of existing, commercially available, low-cost equipment, the ARGALI system may function as a cost effective diagnostic system which will be of clinical significance for glaucoma screening, diagnosis and analysis.

The invention may be expressed as a method, or as an apparatus for carrying out the method, or as a computer program product (such as a tangible recording medium) carrying program instructions readable by a computer to cause the computer to carry out the method.

BRIEF DESCRIPTION OF THE DRAWINGS

An embodiment of the invention will now be described, for the sake of example, only, with reference to the following drawings in which.

DETAILED DESCRIPTION OF THE EMBODIMENTS

1. Explanation of the Method

Figure 1:
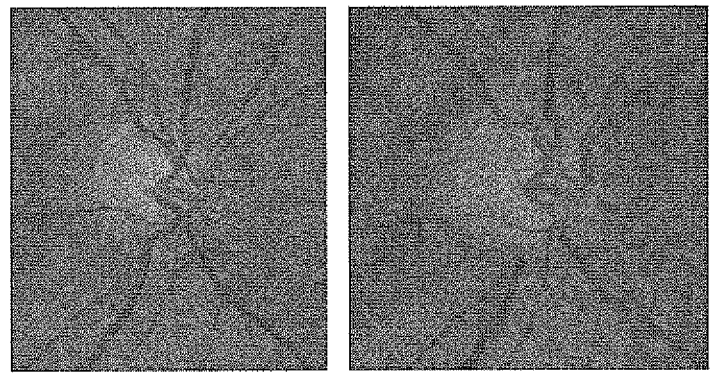
FIG. 1 is retinal photographs showing progression of a (a) normal to (b) large (glaucomatous) optic CDR over the course of 10 years.
Figure 2:
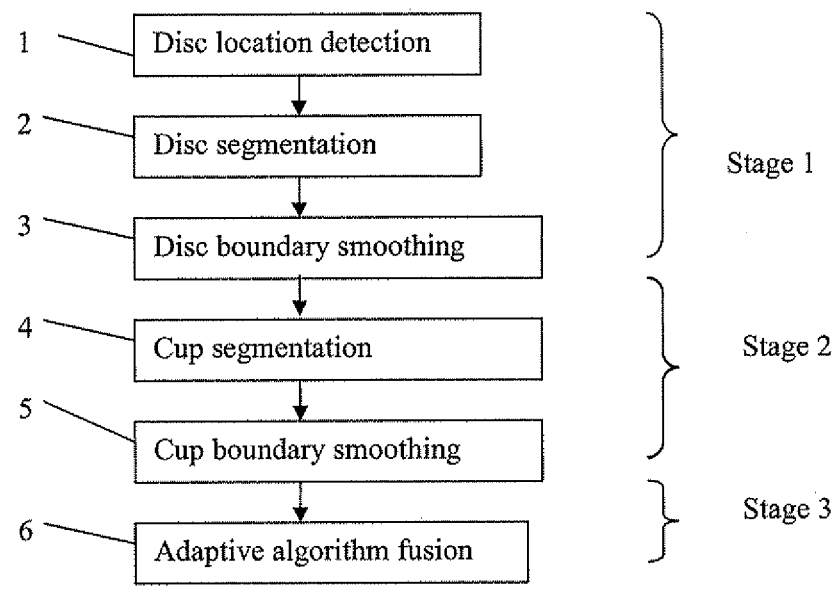
FIG. 2 is a flow diagram of the steps of a method which is an embodiment of the invention.
Figure 3:
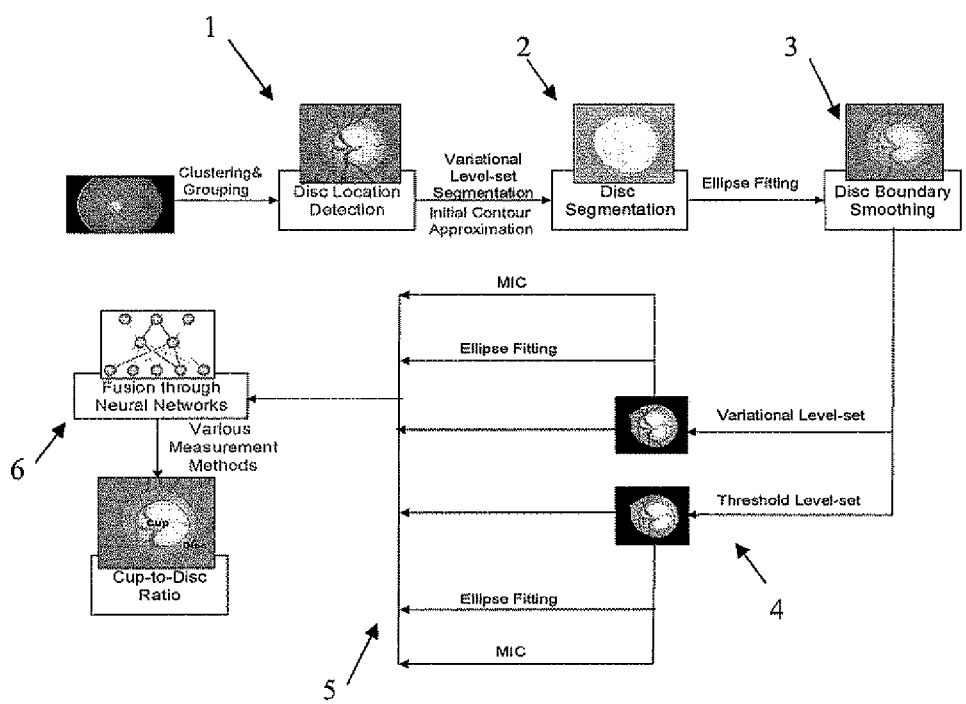
FIG. 3 is a schematic flow diagram of the method of FIG. 2.

A method which is an embodiment of the invention will now be described with reference to FIG. 2, which shows the overall steps of the method. FIG. 3 shows the same process schematically, with corresponding steps given the same reference numerals. The embodiment is referred to here as "ARGALI".

The input to the method is a fundus image. Stage 1 of the method is to identify the disc, in three steps. Initially, the image is subject to an optional step of finding the approximate location of the disc (step 1) in the form of a region of interest. Then a segmentation step (step 2) is performed by a variational level-set approach, which is based on global optimization concepts, to segment the disc boundary and extract the optic disc region from the retinal image. Then a step (step 3) of smoothing the boundary is carried out.

In stage 2 of the method, the optic cup is identified in two steps. Segmentation of the optic cup is more challenging than the optic disc due to the optic cup's interweavement with blood vessel and surrounding tissues. Step 4 of the method is to do this using a multi-modal approach. First, a color histogram analysis of the image is carried out, and two level-set algorithms are applied to segment the cup boundary in respective ways. In step 5, the two segmented cups are each smoothed in two separate ways, one making use of ellipse fitting and another in which a maximum inscribed fitted circle is used.

Finally, in step 6, which is a third stage of the method, an adaptive model (such as a neural network) fuses the cup-to-disc calculation results from the level-set algorithms of steps 2 and 4, as well as the results after the different smoothing processes of steps 3 and 5. This neural network has been produced using a learning mechanism which integrates knowledge embedded in clinical practice, and provides an optimal CDR for the glaucoma screening, diagnosis and analysis.

Steps 1 to 6 will now be described in more detail.

(i) Stage 1: Disc segmentation and boundary smoothing (steps 1 to 3)

In step 1, a region of interest including the optic disc is first delineated. This step is optional, since disc and cup extraction can alternatively be performed on the entire image. However, since the optic disc generally occupies less than 5% of the pixels in a typical retinal fundus image, localizing the ROI (Region of Interest) helps to reduce the computational cost as well as improve segmentation accuracy. The optic disc region is usually of a brighter pallor or higher color intensity than the surrounding retinal area. This characteristic is exploited through automatically selecting the 0.5% of the pixels in the image with the highest intensity. Next, the retinal image is subdivided into 64 regions, and an approximate ROI centre is selected based on the region containing the highest number of pre-selected pixels. Following this, the ROI is defined as a rectangle around the ROI centre with dimensions of twice the typical optic disc diameter. This is used as an initial boundary for the optic disc segmentation In step 2, the method employs a variational level set algorithm (see reference [5]) on the ROI to segment the optic disc. The advantage of using a variational level set is that it delineates the re-initialization by introducing an energy function consisting of an internal term that keeps the level set function near the signed distance function, as well as an external term that moves the contours towards objects in an image. The red channel was utilized as it was observed that better contrast existed between the optic disc and non-disc area than for the other channels.

During segmentation, however, it was observed that the detected contour was often uneven due to the influence of blood vessels across the boundary of the disc, causing inaccuracies in the detected disc, known as leakages.

Despite the use of a global optimization technique, the disc boundary detected by level-set in this step may not represent the actual shape of the disc, as the disc boundary can be affected by a remarkable number of blood vessels entering the disc. This can often result in sudden changes in curvature. TO avoid this, in step 3 ellipse fitting is applied to reshape the obtained disc boundary. Ellipse fitting helps to smooth the sudden changes of curvature in the boundary caused by blood vessels and helps to find the ellipse with minimum error to fit the disc boundary.

(ii) Stage 2: Cup segmentation and boundary smoothing (steps 4 and 5)

Obtaining the cup boundary is more challenging than disc segmentation due to the cup's intensive interweavement with blood vessels and surrounding tissues. Furthermore, the transition between the cup and the rim is often not as prominent as that at the disc boundary.

In step 4, both the variational level-set algorithm [5] and a threshold level-set algorithm are applied to derive respective estimates of the cup boundary. In the threshold level-set approach, the cup boundary is determined by first obtaining an estimate of the cup boundary via threshold techniques, and then applying the level-set method (see appendix) to optimize the detected cup contour. Specifically, the green channel of the extracted optic disc is selected for further segmentation due to the optimum observed contrast between the cup and disc boundaries in this channel. From the pixel intensity information in this channel, a threshold value which segments out the pixels corresponding to the top ⅓ of the grayscale intensity was used to define the initial contour. This was found to produce acceptable results for the initial estimate. Next, the level set formulation discussed earlier was employed to the initial contour to segment the optic cup.

In step 5, each of the outputs of step 4 is further separately smoothed, first using ellipse fitting, and separately using maximum inscribed circle (MIC) matching to eliminate some of the obtained cup boundary's sudden changes in curvature. Maximum inscribed circle matching is especially useful when portions of blood vessels in the neuroretinal rim outside the cup are included within the detected boundary.

Figure 4:
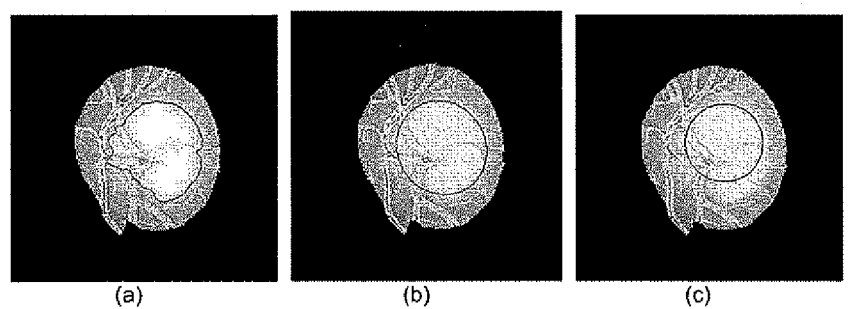
FIG. 4 shows three cup boundaries generated after blood vessel extraction in a step of the method of FIG. 2: (a) the threshold level-set segmented boundary, (b) a smoothed boundary produced using MIC fitting, and (c) a smoothed boundary produced using ellipse fitting.

Some different segmented boundaries of an optic cup are shown in FIG. 4. FIG. 4(a) is the direct result of segmentation by the threshold level-set method of step 4, while FIGS. 4(b) and (c) respectively show the results of ellipse fitting and MIC matching applied to this segmentation.

Stage 3: Neural Network Intelligent Fusion (step 6)

A multi-layer neural network is used in step 6 to fuse the CDR calculation results after obtaining the disc and cup boundaries output in steps 2, 3, 4 and 5. The output of the neural network is the optimal CDR value of the system. The network is produced by a learning algorithm using a large collection of retinal fundus images. CDR may be "vertical CDR" (based on diameters in the vertical direction) or "horizontal CDR". Although the present invention is applicable to both, clinically vertical CDR is much more common, and the present embodiment was tested using vertical CDR since only vertical CDR was available for the collection of retinal fundus images.

2. Experimental Results

Retinal fundus image sets of 2000 patients from the Singapore Eye Research Institute were collected. Out of these, 149 are glaucoma patients. Currently, images of 23 randomly chosen glaucoma patients were processed via the embodiment described earlier.

The neural network of the embodiment was produced by a learning algorithm using a large collection of retinal fundus images from 2000 patients collected from the Singapore Eye Research Institute, and corresponding target CDR values generated by clinical practitioners which were taken to be "ground truth". In this way, this neural network learning mechanism integrates the knowledge embedded in the clinical practice and provides an optimal CDR for the glaucoma screening, diagnosis and analysis. In the experiment, a feed-forward neural network employing multilayer perceptrons (8 input nodes, 15 hidden nodes and 1 output node) with a back-propagation learning architecture was utilized to learn the optimal combination of inputs to output via training with input-output pairs. The network was defined with 15 hidden neurons and eight input nodes. The outputs of the hidden neurons were the inputs of the output neuron. The weights of the connections in the network were trained such that the output node gave the target CDR when the corresponding input data was applied to the input nodes. In order to reduce local minima effects, a momentum term was also included in the network learning algorithm.

Figure 5:
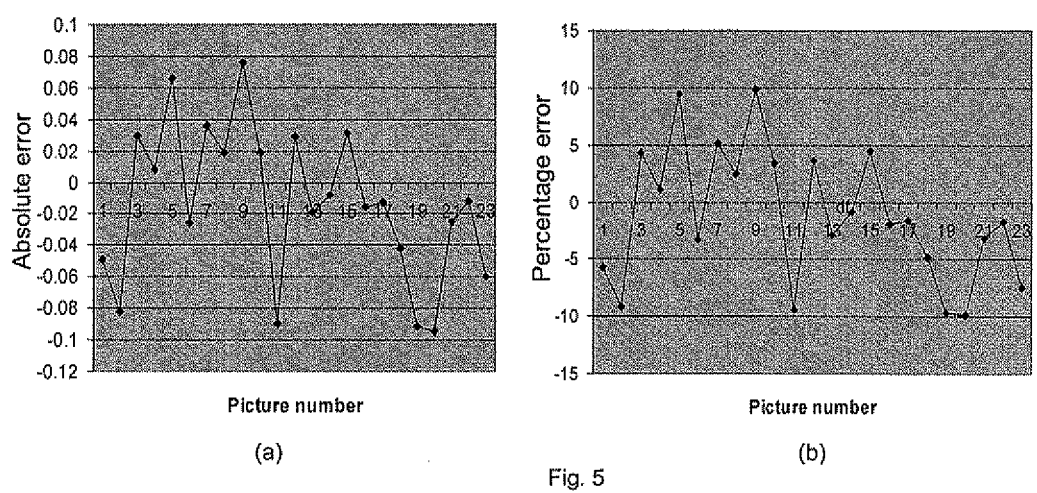
FIG. 5 shows experimental results consisting of data indicating (a) absolute error in the CDR value produced by the embodiment of FIG. 2 for each of 23 patients, and (b) the distribution of the percentage error for the 23 patients

From the processed images, the vertical CDR using the embodiment, "$CDR_{ARGALI}$", is calculated. The clinician assessment of the CDR from the Singapore Eye Research Institute is treated as the ground truth, "$CDR_{GT}$", and as the reference standard against which the performance of the ARGALI system is measured. Performance metrics consisting of the error distributions are shown in FIG. 5 as absolute values (FIG. 5(*a*)) and percentages (FIG. 5(*b*)). The statistics (means and standard deviations of $E_{abs} = CDR_{ARGALI} - CDR_{GT}$ and $E_\% = E/CDR_{GT} \times 100\%$) are presented in Table II.

TABLE II

Statistics of the absolute and percentage error performance

| Statistic | Value |
| --- | --- |
| Mean of absolute error $E_{abs}$ | −0.013623374 |
| Standard deviation of absolute error $E_{abs}$ | 0.048974106 |
| Mean of percentage error $E_\%$ | −1.213994124 |
| Standard deviation of percentage error $E_\%$ | 5.902529066 |

It can be seen that CDR obtained through ARGALI, $CDR_{ARGALI}$, achieves an average 98.6% consistency with the clinical ground truth, $CDR_{GT}$. The mean and standard deviation of the absolute error rates are −0.014 and 0.049. The mean and standard deviation of the percentage error rates are −1.214% and 5.903%. Using the clinically derived CDR value of 0.6 as the threshold to determine whether a patient has glaucoma, the results show that ARGALI achieves 100% accuracy for the diagnosis for the 23 patients.

In future enhancements of the embodiment, it is intended that the rest of the images will also be processed. As and when more retinal images from SERI are made available, they would also be processed and their results included. In this way, the knowledge database continually increases, improving the quality of the obtained results. Already, we have tested the system using 3288 images, instead of 2000.

3. Comparison with the Method with Prior Art Methods of [1]-[4]

The following tables compare ARGALI with prior art methods [1]-[4]. Table III compares the characteristics of the various approaches. Table IV compares the performance of ARGALI with prior art techniques [1]-[4]. Table V compares the methodologies of ARGALI with prior art techniques [1]-[4].

TABLE III

Comparison of characteristics of ARGALI with prior art methods [1]-[4]

| | Disc Segmentation | Cup Segmentation | Automatic | CDR Experimental results |
| --- | --- | --- | --- | --- |
| Prior Art 1 | Yes | No | Automated | N.A |
| Prior Art 2 | Yes | No | Automated | N.A |
| Prior Art 3 | Yes | Yes | Automated | Yes |
| Prior Art 4 | Yes | Yes | Automated | Yes |
| ARGALI | Yes | Yes | Fully automated | Yes |

TABLE IV

Comparison of performance of ARGALI with prior art methods [1]-[4]

| | Mean Error (%) | Standard Deviation (%) | Data sets | Results |
| --- | --- | --- | --- | --- |
| Prior Art methods [1]-[3] | N.A | N.A | N.A | N.A |
| Prior Art method [4] | −4.33 | 12.59 | Clinical datasets | Good |
| ARGALI | −1.214 | 5.903 | Clinical datasets | Better |

TABLE V

Methodology comparison of ARGALI with prior art method [4]

| | Disc Segmentation | Cup Segmentation | Fusion | Adaptive |
| --- | --- | --- | --- | --- |
| Prior Art 4 | Modified SNAKE | Modified SNAKE | No | No |
| ARGALI | Variational level-set | Variational level-set and threshold level set | Yes | Yes |

From the comparisons made between ARGALI and the prior art methods [1]-[4], it has been shown that the fully automatic ARGALI uses a hybrid approach, intelligent adaptive fusion and achieves better experimental results.

REFERENCES

[1] H. Li, O. Chutatape. A model-based approach for automated feature extraction in fundus images. In Proc. of the 9th IEEE International Conference on Computer Vision, 2003.

[2] Y. Tang, X. Li, A. Freyberg, G. Goch. Automatic segmentation of the papilla in a fundus image based on the C-V model and a shape restraint. In Proc. of the 18th International Conference on Pattern Recognition, 2006.

[3] N. Inoue, K. Yanashima, K. Magatani, T. Kurihara. Development of a simple diagnostic method for the glaucoma using ocular fundus pictures. In Proc. of the 27th IEEE engineering in medicine and biology annual conference, 2005.

Xu, O. Chutatape, E. Sung, C. Zheng, P. C. T. Kuan. Optic disc feature extraction via modified deformable model technique for glaucoma analysis. Pattern Recognition 40 (2007) 2063-2076, 2006.

C. Li, C. Xu, C. Gui, M. D. Fox. Level set evolution without re-initialization: a new variational formulation. In Proc. of the 2005 IEEE Computer Society Conference on Computer Vision and Pattern Recognition, 2005.

APPENDIX

Although the embodiment used the segmentation techniques described above, and a neural network as the adaptive model, the invention is not limited in this respect, and the present appendix is a non-exhaustive list of alternative techniques which may be used in other embodiments of the invention.

(i) Image Segmentation Methods for Steps 2 and 4
a) Clustering Methods

The K-means algorithm is an iterative technique that is used to partition an image into K clusters. The basic algorithm is:
1. Pick K cluster centers, either randomly or based on some heuristic
2. Assign each pixel in the image to the cluster that minimizes the variance between the pixel and the cluster center
3. Re-compute the cluster centers by averaging all of the pixels in the cluster
4. Repeat steps 2 and 3 until convergence is attained (e.g. no pixels change clusters)

In this case, variance is the squared or absolute difference between a pixel and a cluster center. The difference is typically based on pixel color, intensity, texture, and location, or a weighted combination of these factors. K can be selected manually, randomly, or by a heuristic.

This algorithm is guaranteed to converge, but it may not return the optimal solution. The quality of the solution depends on the initial set of clusters and the value of K.

b) Histogram-Based Methods

Histogram-based methods are very efficient when compared to other image segmentation methods because they typically require only one pass through the pixels. In this technique, a histogram is computed from all of the pixels in the image, and the peaks and valleys in the histogram are used to locate the clusters in the image. Color or intensity can be used as the measure.

A refinement of this technique is to recursively apply the histogram-seeking method to clusters in the image in order to divide them into smaller clusters. This is repeated with smaller and smaller clusters until no more clusters are formed.

One disadvantage of the histogram-seeking method is that it may be difficult to identify significant peaks and valleys in the image.

c) Edge Detection Methods

Edge detection is a well-developed field on its own within image processing. Region boundaries and edges are closely related, since there is often a sharp adjustment in intensity at the region boundaries. Edge detection techniques have therefore been used to as the base of another segmentation technique.

The edges identified by edge detection are often disconnected. To segment an object from an image however, one needs closed region boundaries. Discontinuities are bridged if the distance between the two edges is within some predetermined threshold.

d) Region Growing Methods

The first region growing method was the seeded region growing method. This method takes a set of seeds as input along with the image. The seeds mark each of the objects to be segmented. The regions are iteratively grown by comparing all unallocated neighboring pixels to the regions. The difference between a pixel's intensity value and the region's mean, δ, is used as a measure of similarity. The pixel with the smallest difference measured this way is allocated to the respective region. This process continues until all pixels are allocated to a region.

Seeded region growing requires seeds as additional input. The segmentation results are dependent on the choice of seeds. Noise in the image can cause the seeds to be poorly placed. Unseeded region growing is a modified algorithm that doesn't require explicit seeds. It starts off with a single region A1—the pixel chosen here does not significantly influence final segmentation. At each iteration, it considers the neighboring pixels in the same way as seeded region growing. It differs from seeded region growing in that if the minimum δ is less than a then a predefined threshold T then it is added to the respective region Aj. If not, then the pixel is considered significantly different from all current regions Ai and a new region An+1 is created with this pixel.

One variant of this technique, proposed by Haralick and Shapiro (1985), is based on pixel intensities. The mean and scatter of the region and the intensity of the candidate pixel is used to compute a test statistic. If the test statistic is sufficiently small, the pixel is added to the region, and the region's mean and scatter are recomputed. Otherwise, the pixel is rejected, and is used to form a new region.

e) Level Set Methods

Curve propagation is a popular technique in image analysis for object extraction, object tracking, stereo reconstruction, etc. The central idea behind such an approach is to evolve a curve towards the lowest potential of a cost function, where its definition reflects the task to be addressed and imposes certain smoothness constraints. Lagrangian techniques are based on parameterizing the contour according to some sampling strategy and then evolve each element according to image and internal terms. While such a technique can be very efficient, it suffers from various limitations like deciding on the sampling strategy, estimating the internal geometric properties of the curve, changing its topology, addressing problems in higher dimensions, etc.

The level set method was initially proposed to track moving interfaces by Osher et Sethian in 1988 and has spread across various imaging domains in the late nineties. It can be used to efficiently address the problem of curve/surface/etc. propagation in an implicit manner. The central idea is represent the evolving contour using a signed function, where its zero level corresponds to the actual contour. Then, according to the motion equation of the contour, one can easily derive a similar flow for the implicit surface that when applied to the zero-level will reflect the propagation of the contour. The level set method encodes numerous advantages: it is implicit, parameter free, provides a direct way to estimate the geometric properties of the evolving structure, can change the topology and is intrinsic. Furthermore, they can be used to define an optimization framework as proposed by Zhao, Merriman & Osher in 1996. Therefore, one can conclude that it is a very convenient framework to address numerous applications of computer vision and medical image analysis.

f) Graph Partitioning Methods

The "normalized cuts" method was first proposed by Shi and Malik in 1997. In this method, the image being segmented is modeled as a weighted undirected graph. Each pixel is a node in the graph, and an edge is formed between every pair of pixels. The weight of an edge is a measure of the similarity between the pixels. The image is partitioned into disjoint sets (segments) by removing the edges connecting the segments. The optimal partitioning of the graph is the one that minimizes the weights of the edges that were removed (the "cut"). Shi's algorithm seeks to minimize the "normalized cut", which is the ratio of the "cut" to all of the edges in the set.

g) Watershed Transformation

The Watershed transformation considers the gradient magnitude of an image as a topographic surface. Pixels having the highest gradient magnitude intensities (GMIs) correspond to watershed lines, which represent the region boundaries. Water placed on any pixel enclosed by a common watershed line flows downhill to a common local intensity minima (LMI). Pixels draining to a common minimum form a catchment basin, which represent the regions.

h) Model based Segmentation

The central assumption of such an approach is that structures of interest/organs have a repetitive form of geometry. Therefore, one can seek for a probabilistic model towards explaining the variation of the shape of the organ and then when segmenting an image impose constraints using this model as prior. Such a task involves (i) registration of the training examples to a common pose, (ii) probabilistic representation of the variation of the registered samples, and (iii) statistical inference between the model and the image. State of the art methods in the literature for knowledge-based segmentation involve active shape and appearance models, active contours and deformable templates and level-set based methods.

i) Multi-Scale Segmentation

Image segmentations are computed at multiple scales in scale-space and sometimes propagated from coarse to fine scales; see scale-space segmentation.

Segmentation criteria can be arbitrarily complex and may take into account global as well as local criteria. A common requirement is that each region must be connected in some sense.

2. Adaptive models for performing the fusion step 6 a) SVM (Support Vector Machine)

Support vector machines (SVMs) are a set of related supervised learning methods used for classification and regression. They belong to a family of generalized linear classifiers. They can also be considered a special case of Tikhonov regularization. A special property of SVMs is that they simultaneously minimize the empirical classification error and maximize the geometric margin; hence they are also known as maximum margin classifiers.

Support vector machines map input vectors to a higher dimensional space where a maximal separating hyperplane is constructed. Two parallel hyperplanes are constructed on each side of the hyperplane that separates the data. The separating hyperplane is the hyperplane that maximizes the distance between the two parallel hyperplanes. An assumption is made that the larger the margin or distance between these parallel hyperplanes the better the generalisation error of the classifier will be.

b) Neural Networks

A Neural Network is an interconnected group of artificial neurons that uses a mathematical or computational model for information processing based on a connectionistic approach to computation. In most cases an ANN is an adaptive system that changes its structure based on external or internal information that flows through the network.

In more practical terms neural networks are non-linear statistical data modeling or decision making tools. They can be used to model complex relationships between inputs and outputs or to find patterns in data.

c) Boosting

Boosting is a general method of producing a very accurate prediction rule by combining rough and moderately inaccurate "rules of thumb". A weak learner is defined to be a classifier which is only slightly correlated with the true classification. In contrast, a strong learner is a classifier that is arbitrarily well-correlated with the true classification.

While boosting is not algorithmically constrained, most boosting algorithms follow a template. Typically boosting occurs in iterations, by incrementally adding weak learners to a final strong learner. At every iteration, a weak learner learns the training data with respect to a distribution. The weak learner is then added to the final strong learner. This is typically done by weighting the weak learner in some manner, which is typically related to the weak learners accuracy. After the weak learner is added to the final strong learner, the data is reweighted: examples that are misclassified gain weight and examples that are classified correctly lose weight (some boosting algorithms will actually decrease the weight of repeatedly misclassified examples, e.g. boost by majority and BrownBoost). Thus, future weak learners will focus more on the examples that previous weak learners misclassified.

The main variation between many boosting algorithms is their method of weighting training data points and hypotheses. AdaBoost is very popular and perhaps the most significant historically as it was the first algorithm that could adapt to the weak learners. However, there are many more recent algorithms such as LPBoost, TotalBoost, BrownBoost, MadaBoost, LogitBoost, and others. Many boosting algorithms fit into the AnyBoost framework, which shows that boosting performs gradient descent in function space using a convex cost function.

d) Bootstrap Aggregating

Bootstrap aggregating (bagging) is a meta-algorithm to improve classification and regression models in terms of stability and classification accuracy. Bagging also reduces variance and helps to avoid overfitting. Although this method is usually applied to decision tree models, it can be used with any type of model. Bagging is a special case of the model averaging approach.

Given a standard training set D of size N, we generate L new training sets Di also of size N' (N'<N) by sampling examples uniformly from D, and with replacement. By sampling with replacement it is likely that some examples will be repeated in each Di. If N'=N, then for large N the set Di expected to have 63.2% of the examples of D, the rest being duplicates. This kind of sample is known as a bootstrap sample. The L models are fitted using the above L bootstrap samples and combined by averaging the output (in case of regression) or voting (in case of classification). One particular interesting point about bagging is that, since the method averages several predictors, it is not useful for improving linear models.

What is claimed is:

1. A method performed by a computer for obtaining a CDR value from a single 2D retinal fundus photograph, comprising the steps of:
   (i) receiving, by the computer, the single 2D retinal fundus photograph;
   (ii) performing, by the computer, optic disc segmentation; wherein said optic disc segmentation comprises deriving an optic disc region of the single 2D retinal fundus photograph received in step (i);
(iii) performing, by the computer, optic cup segmentation based on said single 2D retinal fundus photograph; wherein said optic cup segmentation comprises deriving an optic cup region of the single 2D retinal fundus photograph received in step (i); and
(iv) inputting data derived from the optic disc segmentation and data derived from the optic cup segmentation into an adaptive model operative to generate a CDR value, wherein the adaptive model is obtained by an automatic learning algorithm using a database of retinal fundus images.

2. A method according to claim 1 in which, following said step (ii), the result of the optic disc segmentation is subject to a smoothing step to produce smoothed disc segmentation data which is employed in said step (iii), and as data input to said adaptive model.

3. A method according to claim 1 in which, following said step (iii), one or more smoothing algorithms are applied to data output from said optic cup segmentation step (iii), to generate respective sets of smoothed optic cup data, said set or sets of smoothed optic cup data being input to said adaptive model in step (iv).

4. A method according to claim 3 in which there are a plurality of said smoothing algorithms, generating a plurality of respective sets of smoothed optic cup data which are input to said adaptive model in step (iv).

5. A method according to claim 3 in which both said smoothed optic cup data and said data output from said optic cup segmentation step (iii) are input to said adaptive model.

6. A method according to claim 1 in which said step (ii) of optic disc segmentation includes a preliminary step of identifying a region-of-interest in said fundus photograph based on the intensity of points in the photograph.

7. A method according to claim 1 in which said step: (ii) of optic disc segmentation employs a variational level set algorithm.

8. A method according to claim 1 in which said step (iii) of optic cup segmentation includes a first sub-step of estimating the cup boundary using a threshold technique, followed by a second sub-step employing a level set technique.

9. A method according to claim 1 in which said step (iii) of optic cup segmentation is performed by a plurality of methods, each method generating a respective optic cup segmentation, step (iv) including inputting data derived from each of these optic cup segmentations into the adaptive model.

10. A method according to claim 1 in which the fundus photograph contains a plurality of colour components, and at least one of said segmentation steps (ii) and (iii) is performed using only a single color component of the colour photograph.

11. A method according to claim 1 in which said adaptive model is a multi-layer neural network.

12. A method according to claim 1 including a preliminary stage of training said adaptive model using a training set comprising target CDR values generated by a clinician.

13. An apparatus for obtaining a CDR value from a single 2D retinal fundus photograph, comprising a processor and a data storage device storing computer program instructions operative when performed by the processor to cause the processor to perform the steps of:
(i) receiving the single 2D retinal fundus photograph;
(ii) performing optic disc segmentation; wherein said optic disc segmentation comprises deriving an optic disc region of the single 2D retinal fundus photograph received in step (i);
(iii) performing optic cup segmentation based on said single 2D retinal fundus photograph; wherein said optic cup segmentation comprises deriving an optic cup region of the single 2D retinal fundus photograph received in step (i); and
(iv) inputting data derived from the optic disc segmentation and data derived from the optic cup segmentation into an adaptive model operative to generate a CDR value, wherein the adaptive model is obtained by an automatic learning algorithm using a database of retinal fundus images.

14. An apparatus according to claim 13 in which the processor is arranged, following said step (ii), to smooth the result of the optic disc segmentation to produce smoothed disc segmentation data which is employed as data input to said adaptive model.

15. An apparatus according to claim 13 in which the processor is arranged, following said step (iii), to perform one or more smoothing algorithms to data output from said optic cup segmentation step (iii), to generate respective sets of smoothed optic cup data, and to input said set or sets of smoothed optic cup data to said adaptive model in step (iv).

16. An apparatus according to claim 15 in which the processor is arranged to perform a plurality of said smoothing algorithms, generating a plurality of respective sets of smoothed optic cup data which are input to said adaptive model in step (iv).

17. An apparatus according to claim 15 in which both said smoothed optic cup data and said data output from said optic cup segmentation step (iii) are input to said adaptive model.

18. An apparatus according to claim 13 in which said processor is arranged, as part of said step (ii) of optic disc segmentation, to perform a preliminary step of identifying a region-of-interest in said fundus photograph based on the intensity of points in the photograph.

19. An apparatus according to claim 13 in which said processor is arranged to employ a variation level set algorithm in step (ii) of optic disc segmentation.

20. An apparatus according to claim 13 in which said processor is arranged, in step (iii), to perform a first sub-step of estimating the cup boundary using a threshold technique, followed by a second sub-step employing a level set technique.

21. An apparatus according to claim 13 in which said processor is arranged, to perform said step (iii) of optic cup segmentation by a plurality of methods, each method generating a respective optic cup segmentation, step (iv) including inputting data derived from each of these optic cup segmentations into the adaptive model.

22. An apparatus according to claim 13 in which the processor is arranged to receive said fundus photograph as a plurality of colour components, and to perform at least one of said segmentation steps (ii) and (iii) using only a single color component of the colour photograph.

23. An apparatus according to claim 13 in which said adaptive model is a multi-layer neural network.

24. A non-transitory computer program product on which are stored program instructions readable by a computer to cause the computer to carry out the method of:
(i) receiving a single 2D retinal fundus photograph;
(ii) performing optic disc segmentation; wherein said optic disc segmentation comprises deriving an optic disc region of the single 2D retinal fundus photograph received in step (i);
(iii) performing optic cup segmentation based on said single 2D retinal fundus photograph; wherein said optic cup segmentation comprises deriving an optic cup region of the single 2D retinal fundus photograph received in step (i); and (iv) inputting data derived from the optic disc segmentation and data derived from the optic cup segmentation into an adaptive model operative to generate a CDR value, wherein the adaptive model is obtained by an automatic learning algorithm using a database of retinal fundus images.

* * * * *